United States Patent [19]

Guggenbuhl et al.

[11] Patent Number: 5,307,817
[45] Date of Patent: May 3, 1994

[54] BIOTELEMETRY METHOD FOR THE TRANSMISSION OF BIOELECTRIC POTENTIAL DEFFERENCES, AND A DEVICE FOR THE TRANSMISSION OF ECG SIGNALS

[75] Inventors: Walter Guggenbuhl, Stäfa; Fritz Grogg, Zürich, both of Switzerland

[73] Assignee: MEDESE AG, Zürich, Switzerland

[21] Appl. No.: 598,685

[22] PCT Filed: Jan. 23, 1990

[86] PCT No.: PCT/CH90/00014
§ 371 Date: Oct. 25, 1990
§ 102(e) Date: Oct. 25, 1990

[87] PCT Pub. No.: WO90/08501
PCT Pub. Date: Aug. 9, 1990

[30] Foreign Application Priority Data

Jan. 27, 1989 [CH] Switzerland ............ 255/89

[51] Int. Cl.$^5$ .................................. A61B 5/0402
[52] U.S. Cl. ................................. 128/696; 128/908; 128/710
[58] Field of Search ............... 128/696, 710, 908, 903, 128/904, 699

[56] References Cited

U.S. PATENT DOCUMENTS

| | | | |
|---|---|---|---|
| 3,646,606 | 2/1972 | Buxton et al. | |
| 3,709,212 | 1/1973 | Koeblitz | 128/696 |
| 3,742,947 | 7/1973 | Hashem | 128/696 |
| 3,910,257 | 10/1975 | Fletcher et al. | |
| 3,915,154 | 10/1975 | Cosentino | 128/696 |
| 3,986,498 | 10/1976 | Lewis | 128/696 |
| 4,243,045 | 1/1981 | Maas | 128/419 PT |
| 4,530,365 | 7/1985 | Harada et al. | 128/696 |
| 4,627,441 | 12/1986 | Martin | 128/696 |
| 4,680,708 | 7/1987 | Ambos et al. | 128/702 |
| 4,683,441 | 7/1987 | Naylor | 128/696 |
| 4,742,831 | 5/1988 | Silvian | 128/710 |
| 4,791,933 | 12/1988 | Asai et al. | 128/696 |
| 4,793,361 | 12/1988 | DuFault | 128/696 |
| 4,858,617 | 8/1989 | Sanders | 128/696 |
| 4,889,134 | 12/1989 | Greenwold et al. | 128/696 |
| 4,957,109 | 9/1990 | Groeger et al. | 128/901 |

Primary Examiner—Kyle L. Howell
Assistant Examiner—Kennedy J. Schaetzle
Attorney, Agent, or Firm—Egli International

[57] ABSTRACT

To obtain optical one-way transmission of bioelectrical potential differences between electrodes placed on a patient and the evaluation apparatus, one of the electrodes placed on the patient is designated as the reference electrode. The potentials of all the other electrodes are referred to this electrode, and the signals derived from the potential differences so obtained are amplified, multiplexed, converted analog/digital and transmitted in coded form. At least one of the potential differences recorded by the evaluation apparatus is derived from the difference between two transmitted signals. The number of signals transmitted can thus be less than the number of potential differences recorded. This process is particularly useful for transmitting electrocardiogram signals (ECG signals) to an ECG apparatus which produces twelve standard derivatives. The optical transmission can also be performed by an optical fibre. The device comprises an emitting part, preferably provided with several light-emitting elements, which forms a self-contained apparatus to be carried by the patient and a receiving part, preferably provided with several light-receiving elements arranged at fixed places in the surroundings.

8 Claims, 3 Drawing Sheets

BIOTELEMETRY METHOD FOR THE TRANSMISSION OF BIOELECTRIC POTENTIAL DEFFERENCES, AND A DEVICE FOR THE TRANSMISSION OF ECG SIGNALS

The invention relates to a biotelemetry method for the transmission of bioelectric potential differences, occurring between more than two electrodes applied on a patient, from the patient to an evaluator that is intended and designed for processing and recording bioelectric potential differences, the transmission of the signals between the patient and the evaluator being effectuated as electromagnetic and particularly optical one-way connection from the patient to the evaluator, while there is no electric connection between the electrodes and the evaluation device, in accordance with the preamble of claim 1, as well as a device for performing this method in an ECG system.

An electrocardiogram (ECG) is the recording of the variation in time of heart action tensions in a living being, in general in a human patient. For further definitions see DIN 13401 (January 1953).

The analysis of the ECG supplies the physician with important data on the heart function of the patient. The ECG signals are picked up at ECG electrodes applied on the patient and arranged at the patient in the usual way for obtaining the so-called standard derivations ("left arm, right arm, left foot, right foot, chest position 1 to 6").

In this process, up to ten cables are connected to the patient, which connect the ECG electrodes with the ECG device, where the ECG signals are processed and recorded. These cables constitute a hindrance to the patient and render the execution of an exercise ECG, for instance if the response of the patient's heart to physical exercise is checked on an ergometer, more difficult: the patient has only very limited possibilities of movement, not least because the ECG electrodes fall off if due to the weight and the stiffness of the cables they are pulled on, or if the patient is moving about violently. Also the psychological strain on the patient, who is linked to a mains operated device via electric leads and who reacts with fear of an electric shock, is not to be disregarded. The effect of this psychological strain can combine itself with the effect of the real physical strain, which subsequently falsifies the examination of the heart function.

For this reason, there exists a need for non-electric and, if necessary, for an immaterial ("wireless") connection between the ECG electrodes applied on the patient and the ECG device: this non-electric connection is to easily replace the usual connection by means of electric leads. In other words, there is a need for a non-electric transmission method for ECG signals adapted to the circumstances of the ECG recording from the ECG electrodes applied on a patient to the ECG device that processes and records the ECG signals.

There is also a need for a device to whose inputs the ECG electrodes applied on the patient are connected in exactly such a way as though they were connected to the ECG device, and whose outputs are connected to the inputs of the ECG device in exactly such a way as though they were the ECG electrodes applied on the patient. By way of this device, customarily designed and arranged ECG electrodes are to be connected with a customary ECG device, the connection having to be non-electric and, if necessary, immaterial.

Under these conditions, it is obvious to devise a connection between the ECG electrodes and the ECG device by means of electromagnetic waves. Such a connection requires a transmitting unit, a transmission link, and a receiving unit. The transmitting unit needs to be carried by the patient, otherwise the patient would be linked with the transmitting unit via electrode cables, which must be rejected as inconsistent and inappropriate. However, evidently the hindrance for the patient to be eliminated is not neutralized, until the transmitting part can be carried easily by the patient. In addition, the transmitting unit must meet the usual requirements in regard to safety of the patient and defibrillation stability (defibrillation is a measure against cardiac flutter or fibrillation). Besides, the considered connection must be able to transmit a great data flow.

In general, telemetry systems for biosignals are already known. From the article by N. Kudo, K. Shimizu and G. Matsumoto "Optical biotelemetry using indirect light transmission" on pages 55–58 of "Biotelemetry IX" (1987, published by H. P. Kimmich and M. R. Neuman) the transmission of bioelectric signals from electrodes applied on a patient to an evaluator is known, in particular, to an ECG device that processes and records the signals. In this process, the transmission of the signals is performed optically, if necessary, in the infrared range, and as one-way link from the electrodes to the evaluator, and no electric connection between the electrodes and the evaluator is established.

It is a disadvantage of this known transmission method that the measuring values are transmitted as analog values: the analog measuring values obtained at the patient are modulated as pulse intervals, converted, multiplexed, transmitted, demultiplexed and demodulated, so that in the end analog values are available again. Such a procedure does not permit the application of modern techniques for the reduction of the liability to disturbances of the transmission and, if necessary, for the correction of transmission errors, which are known in the field of digital data transmission.

This known transmission method is notably disturbed, in particular, by the light of AC light sources, i.e. by the 50 Hz-hum and the 100 Hz-noise of fluorescent tubes, and also by their harmonic oscillations.

Besides, another disadvantage of this known transmission method is that the transmitted analog values are by no means adapted to the circumstances of the ECG recording with an ECG device that supplies the twelve standard derivations, causing that the known optical transmission system cannot be used easily instead of the customary connection by means of electric leads. In particular, the transmitted values are not fed to the ECG device in an isochronic manner, because the sampling required for the multiplexing supplies mutually time-displaced signals on the various channels. In the case of the known transmission method, the necessary correction of this time displacement is not provided.

It is a further disadvantage of this known transmission method that for each of the potential differences between specifically selected electrodes, which are of interest to the physician, a channel of the telemetry system is needed so that the number of recorded potential differences equals the number of transmission channels or of signals transmitted. In the system described in the quoted article, only three channels for signals corresponding to potential differences are provided (the fourth channel is assigned to a temperature-related signal). When using this art in systems intended for recording a greater number of potential differences, such as in a ECG system with twelve standard derivations, twelve transmission channels would be required.

Besides, there exists a need for a method and a device for biotelemetry that make it possible to offer not only ten transmission channels as for electrocardiography with twelve standard derivations but twenty-two to twenty-four channels as needed for electroencephalography.

Therefore, it is the object of this invention to remedy the disadvantages of the known transmission method in a biotelemetry method of the kind mentioned above, and in particular in a transmission method via a great number of channels, for example with eight channels for the transmission of electrocardiogram signals (ECG signals) to an ECG device supplying twelve standard derivations, or with twenty-two to twenty-four channels for the transmission of electroencephalography signals (EEG signals), and in particular to reduce the required number of transmission channels.

According to the invention, this object is accomplished in that at the patient's end one of the electrodes is designated as reference electrode to which the potentials of all the remaining electrodes are referred, the signals that were formed by the corresponding potential difference between the remaining electrodes and the reference electrode, are amplified, multiplexed, A/D-converted and transmitted in an encoded way, and at least one of the potential differences to be recorded in the evaluator was obtained from the difference between two transmitted signals.

For the forming of potential differences at the patient's end, preferably all remaining electrodes are paired with the reference electrode (in the case of four electrodes in a way analog to a three-phase star connection), while at the end of the evaluator the potential differences to be recorded are for the one part obtained from the difference between one pair of transmitted signals each (in the case of three potential differences in a way analog to a three-phase delta connection) and for the other part directly from one transmitted signal each (in the case of three potential differences in a way analog to a three-phase star connection against ground potential) so that the number of transmitted signals is smaller than the number of recorded potential differences.

Preferably, the signals converted from analog to digital are encoded in the Manchester code or as frequency shift keying and preferably equipped with additional information for error protection.

Preferably, for the transmission of electrocardiogram signals (ECG signals) to an ECG device supplying twelve standard derivations, in the course of which at least ten ECG electrodes are applied on the patient in the customary way for obtaining the standard derivations ("left arm, right arm, left foot, right foot, chest position 1 to 6"), the method according to the invention is characterized in that two specific ECG electrodes ("left foot, right foot") are defined as first ("left foot") and second ("right foot") ECG reference electrodes and the remaining ECG electrodes ("left arm, right arm, chest position 1 to 611) as ECG signal electrodes, for each ECG signal electrode the difference between the ECG signal obtained from it and the ECG signal obtained at the first ECG reference electrode ("left foot") is formed and thus a signal is produced that is freed from the common direct voltage content and from the hum ("common mode rejection"), the second ECG reference electrode ("right foot") is used for the determination of a reference potential at the patient's end, the signals to be transmitted are transmitted in a one-way serial manner by multiplexing them, converting the multiplex signal from analog to digital, and subsequently into an encoded signal to which, if necessary, additional information for error protection is added, with the encoded signal a light beam is modulated, the light beam is sent, transmitted and received, the received light beam is demodulated, the obtained modulation decoded, if necessary, the decoded signal is corrected by means of the additional information for error protection, converted from digital to analog, and demultiplexed in order to obtain transmitted ECG signals, and the transmitted ECG signals are fed to the corresponding inputs ("left arm, right arm, chest position 1 to 6") of the ECG device ("right foot, left foot"), while the reference potential of the transmitted ECG signals is supplied to the remaining inputs of the ECG device ("right foot, left foot").

Preferably, the transmission is performed optically via an optical cable.

A device for performing the method of the invention in its embodiment designed for the transmission of electrocardiogram signals (ECG signals), said ECG system comprising at least ten ECG electrodes applied on a patient ("left arm, right arm, left foot, right foot, chest position 1 to 6") and an ECG device for twelve standard derivations, while two specific ECG electrodes ("left foot, right foot") are defined as first ("left foot") and second ("right foot") ECG reference electrodes and the remaining ECG electrodes as ECG signal electrodes, is characterized by a transmitting unit, a receiving unit, and at least one optical link in between, the sending unit including:

input protection circuits known per se in ECG systems to which one assigned ECG electrode each can be connected, computing circuits known per se in ECG systems for obtaining the difference between signals from two input protection circuits, one of which is assigned to an ECG signal electrode ("left arm, right arm, chest position 1 to 6") and the other to the first ECG reference electrode ("left foot") so that also each signal difference is assigned to an ECG signal electrode, a connection of the output of the input protection circuit that is assigned to the second ECG reference electrode ("right foot"), with a common ground lead for the computing circuits, a multiplexer for the obtained signal differences, at least one modulatable optotransmitter at whose modulation input the output of the multiplexer is linked via the connection in series of an analog-to-digital converter, an encoder, and, if necessary, a circuit for adding additional information for error protection, and the receiving unit including:

at least one optoreceiver equipped with an output for the output of the modulation of a received light beam, a demultiplexer with an input linked to the output of the optoreceiver(s), if necessary via a connection for correction by means of the additional information for error protection, and then via the connection in series of a decoder and a digital-to-analog converter, and with outputs, each of which is assigned to the signal differences formed in the transmitting unit and carrying a signal that can be fed to a corresponding input ("left arm, right arm, chest position 1 to 6") of the ECG device.

In a preferred embodiment of the device according to the invention, the transmitting unit is designed as independent device that may be carried by the patient. Preferably, at least one and preferably several optotransmitters are arranged on at least one side of the transmitting unit not facing the patient, and at least one and preferentially several optoreceivers are arranged at one or several fixed locations of a room surrounding the patient.

In another preferred embodiment of the device according to the invention, the transmitting unit is designed as independent two-part device with an operating unit and an optotransmitter portable unit, both units capable of being carried by the patient and possessing at least one and preferentially several optotransmitters on at least one side not facing the patient, while at least one and preferentially several optoreceivers are arranged in one or several fixed locations of a room surrounding the patient.

In this invention, there is recognized and used the possibility of forming the 12 standard derivations, in the ECG technology, for the one part directly from 8 signals obtained by referring them to a reference electrode and for the other part by forming of the difference between two signals in the evaluator. The number of displayable "derivations" could, according to this method and if it is of interest to the physician, be increased to up to 36.

In the device according to the invention, this kind of acquisition and transmission of bioelectric potential differences in connection with a ECG system is reached by using two reference electrodes at the transmitting end, one of which ("left foot") is used as reference electrode in the above way and the other ("right foot") for the determination of the electric reference potential of the transmitting unit.

In the method according to the invention, individual "derivations" are calculated from the difference between one pair each of transmitted potential values, which requires a higher accuracy of the transmission channels than with the customary direct transmission of the potential values corresponding to the "derivations". For example, differences of two approximately equal potential values have to be formed, which impairs the relative accuracy of the result. The required higher accuracy of the transmission channels is ensured, in accordance with the invention, by digital transmission with a sufficient number of bits, and could be accomplished in a customary system, e.g. by means of the analog transmitting method described in the quoted article, only at the cost of a high instrumental effort (costs, weight).

In order to reduce the weight of the transmitting unit and the general effort, the method according to the invention, as well as the method known from "Biotelemetry IX", operates with a one-way transmission without receive acknowledgement. In order to attain the highest possible transmission speed and data integrity with lowest possible error liability, the transmission of the method according to the invention is digital and encoded according to an appropriate encoding method, preferentially in the Manchester code or as frequency shift keying (=FSK). It is a particular advantage of these encoding methods that their frequency spectra have no continuous and no effective low-frequency content so that the 50 Hz-hum and the 100 Hz-noise by fluorescent tubes and their harmonic oscillations can be suppressed. Besides, Manchester code and FSK-modulation do not require a synchronization of the receiving clock pulse and the transmitting clock pulse, because they are autosynchronizing at the receiving end and thus guarantee data integrity and low error liability for the receiving end in spite of one-way transmission without receive acknowledgement.

Besides, the transmission of digital data permits adding to them an additional information for error protection, e.g. for the cyclic redundancy check (CRC), for the parity check, or according to the Hamming code. Circuits for the creation of additional information for error protection at the transmitting end and for the execution of the relevant checks at the receiving end are well-known to persons skilled in the art.

The device according to the invention is intended and designed for replacing easily the customary connection cables, while the physician does not have to trained or retrained for using the device according to the invention. The transmitting unit taps the ECG electrodes, produces the ECG signals, amplifies them, converts them to the required shape, and transmits them in a definitely non-electric and, if necessary, in a wireless or cableless way. The receiving unit reproduces the ECG signals and attenuates them to the normal value of real ECG signals picked up directly at the ECG electrodes so that the outputs of the receiving unit can be connected directly to the corresponding inputs of a customary ECG device. The ECG device does not "note" any difference, whether the patient is connected directly by the customary cables or by the device according to the invention, and the ECG recording is the same in both cases.

Besides, the optical transmission preferentially used in the method according to the invention and in the device according to the invention brings on the advantage of not being subject to legal provisions and restrictions in regard to transmitting and receiving licenses.

The method according to the invention, its modifications, and embodiment examples of the device according to the invention are explained hereinafter in further detail by reference to the drawings.

For the explanation of the invention, several requirements to be met at the entry of the device according to the invention need to be discussed first.

At the electric transition between ECG electrodes and the skin of the patient, the transition from the ionic conduction of the body to the electron conduction of the ECG electrode connections takes place. This creates a galvanoelectric direct voltage that may take on several values because of irregularities of the skin and causes a galvanoelectric direct voltage to exist also between two ECG electrodes. It is to be suppressed in signal processing because it is significantly greater than the useful signal of approx. 1 Mv. If the galvanoelectric direct voltage is suppressed as usual only after a preamplification of the ECG signals in the input amplifier, this occasions that these direct voltages are to be amplified in a linear way.

In addition, as little current as possible is to flow by way of the ECG electrodes because it alters the chemical composition of the skin and provokes polarization voltages which may vary a great deal with regard to time. The input currents should remain smaller than 0.1 fA and the input amplifier should have a high input impedance of higher than 2 Mohm.

Due to the patient and his/her environment, aside from the desired useful signals several superimposed disturbing voltages appear at the output of the ECG electrodes, the greatest of which, i.e. the 50 Hz-hum and its harmonic oscillations, appear as common-mode voltage and can be suppressed by means of the appropriate, principally known techniques: a common mode rejection rate (CMRR) of 80 dB is desirable.

The frequency response of ECG signals is of a kind that frequencies above 100 Hz may be neglected, while the ECG signals located within the frequency band from 0.1 Hz to 100 Hz are to be transmitted and processed as distortion-free as possible, both with regard to phase and amplitude.

The inputs of the device according to the invention, and its sensitive input amplifiers are to be protected from overdrive or excitation by high-frequency parasitics. On the other hand, the remaining direct voltage and interference are to be separated from the useful signal, which can be achieved by means of high-pass and low-pass filters with different time constants (approx 3 s and approx 4 Ms). In addition, the inputs of the input amplifiers should bear or be shielded from the high voltage pulses (3 kV during 5 ms) occurring during a defibrillation. This can be achieved in a known manner by way of signal contraction via Zener diodes connected in an anti-serial way: so-called bidirectional Zener diodes developed for these specific aims are for sale.

The patient's safety is to be guaranteed in a legally stipulated manner, e.g. according to the Swiss "SEV-Norm TP62/d", which provides that in the case of a failure of the device 5 mA at the most, and during normal operation 100 fA at the most, may flow through the patient.

For explaining the invention some requirements in regard to the electromagnetic and, in particular, optical transmission need to be discussed, too.

The electromagnetic and, in particular, the optical transmission of the ECG signals could be effectuated in parallel on several channels or serially on one channel only: considerations as regards economic efficiency and portability of the transmitting unit lead to the selection of the serial transmission on one single channel, thus requiring that the signals need to be multiplexed prior to transmission and demultiplexed after the transmission. However, then the frequency band of the signal to be multiplexed must have an upper limit which according to the Shannon theorem does not exceed half of the sampling frequency of the multiplexer: this is achieved by means of a so-called "antialiasing" filter, e.g. a Butterwork filter of the 2nd order with a limit frequency of 180 Hz for a sampling frequency of 600 Hz at the multiplexer.

The transmission in series requires multiplexing, however, customary multiplexers are not able to process the ECG signals in the millivolt range, and their input impedances do not meet the requirements of ECG input amplifiers. In addition, direct voltage contents need to be suppressed in the ECG signals, which—as has been described hereinabove—is done by using filters whose time constant of approximately 3s leads to settling times that are significantly longer than the connecting times of the ECG signal at the multiplexer which, for this reason, has to be arranged after such filters.

For these reasons, the device according to the invention possesses one input amplifier each per ECG signal, and multiplexing is done after the input amplifiers. The possibility of using analog-to-digital converters with integrated multiplexers is an advantage.

In a customary ECG-device, there exists the possibility of tapping the currently needed signals in a bipolar-differential manner by means of difference amplifiers, thus suppressing also the common-mode voltage as against the reference potential ("right foot"). As a consequence, by using the method according to the invention and the device according to the invention the suppression of the common-mode voltage taking place in the ECG device is not effective in suppressing the common-mode contents of the currently evaluated ECG signals which are decisive for transmission. Therefore, the common-mode voltage must, as far this is possible, take place already prior to the transmission of the ECG signals, preferentially in the input amplifiers of the device according to the invention, in order to avoid an overdrive of the transmission channels and of the battery-powered input amplifiers. For this reason, their ground lead is connected with the patient in a high-resistance manner, which is done preferentially at the ECG electrode applied on the right foot of the patient, which is not directly used for purposes of examination: hence, this electrode becomes the second ECG reference electrode ("right foot") and determines the reference potential at the patient's end. At the receiving end, the connection for the second ECG reference electrode ("right foot") is not needed anymore, however, since it exists its potential must not remain undefined, and for this reason it is connected, if necessary, in a high-resistance manner with the reference potential of the receiving unit.

In an ECG device used in a customary way, with ECG electrodes directly connected to it, all ECG signals are available to the ECG device in parallel: the ECG device may at all times access all ECG signals which are referred to the potential of the ECG electrode located at the right foot of the patient (reference potential).

However, when using the method according to the invention and the device according to the invention, the ECG signals are transmitted serially. Since there is no acknowledgement by the receiver to the transmitter stating which signals are currently needed by the ECG device at a certain moment, the ECG signals need to be prepared again in parallel. The simplest solution is to refer all ECG signals prepared at the receiving end to one single common reference voltage, i.e. to the reference potential of the receiving unit. Hence, the connection for the first ECG reference electrode ("left foot") at the receiving end is not needed anymore, however since it exists, its potential must not remain undefined and it is, if necessary, connected with the reference potential of the receiving end in a high-resistance manner.

In existing ECG devices real difference amplifiers are invariably used for the evaluation of the ECG signals, because they need only a small number of them, that is one difference amplifier per ECG signal recorded, for the recording is, if requested, shifted from one to the other ECG signal.

When using the method according to the invention and the device according to the invention, one difference amplifier for each transmitted ECG signal would have to be provided according to this customary procedure, and at its two inputs one operational amplifier (buffer) each would have to be connected in series in order to ensure a very high-resistance input of the amplifier. Thus, a great number of difference and operational amplifiers would be required, bringing on problems in regard to cost and weight. However, since all ECG signals at the transmitting end are invariably referred to the same reference voltage of the first ECG electrode ("left foot"), it is not necessary to use real difference amplifiers. Each ECG signal may be fed to the non-inverting input of an assigned operational amplifier, because it is a high-resistance input. For the correct forming of the desired differences all ECG signals must be equally amplified in their respective operational amplifiers: this is achieved by adjusting the amplification at the other inverting input of the respective operational amplifier. After all, the output of the operational amplifier, which is assigned to the first ECG reference electrode ("left foot"), is connected with the inverting inputs of the operational amplifiers, which are assigned to the other ECG signals.

An advantage of this embodiment is the input amplifier and that signals are available by means of which a carry-along circuit (a so-called bootstrap) can significantly increase the effect of the cable shields. Since for practical reasons it is not possible to shield every input separately, the shield for all inputs is carried along on one and the same potential. This potential is determined in a separate operational amplifier as mean value of selected ECG signals. Because the summation at this operational amplifier is inverting, a second operational amplifier for the inversion of the obtained shield signal is provided.

The requirement that the ECG device should not "note" any difference, whether the patient is connected directly by the customary cables or by the device according to the invention, occasions that the transmitted signals need to be attenuated at the receiving end in the same proportion as they were amplified at the transmitting end. In the receiving unit the corresponding interface between the outputs of the demultiplexer and the inputs of the ECG device is quite simple: the ECG signals at the outputs of the demultiplexer are attenuated in a potentiometer-type resistor in merely such a way that they correspond to the normal values of real ECG signals that are picked up directly at the ECG electrodes, so that they can be fed directly into the respective inputs of a customary ECG device. The noise from the digital-to-analog conversion is eliminated by the low-pass filters included in the ECG device anyway, the high-resistance inputs of the ECG eliminate the problem of the output resistance at the demultiplexer. Besides, as has been mentioned before, both inputs of the ECG device for the ECG reference electrodes ("right foot, left foot") are connected to the reference potential of the receiving unit. Parts of the receiver of this device decribed hereinabove as accessory of a customary ECG system can also be integrated into the ECG device, thus reducing the entire instrumental effort. In general, the effort for the electrical safety of the patient in the receiving unit and in the ECG device can be vastly reduced in relation to the customary embodiment linked galvanically to the patient, because the electromagnetic and, in particular, optical link causes the electrical isolation.

In regard to the two transmission methods in free air or via an optical waveguide, there exist the following possibilities for use of the invention. Both transmitting and receiving unit can be switched over to one or another transmission method by actuation of a changeover switch and thus be used for both transmission methods.

The transmission in free air is particularly suitable if the patient should be capable of moving about freely, for example, as is necessary for ergonometric measurements.

The transmission via an optical waveguide is particularly suitable for application in an operating theater or an intensive care unit where the disturbances of the transmission by light sources can be very heavy. The transmitting unit can be applied on the bed of a bedridden patient. The optical transmission will then be effectuated in a very simply way via a disconnectable plug-in connection of the waveguide at the transmitting unit and at the ECG device, so that the patient can be "connected and disconnected" rapidly and without difficulty. The transmission via a waveguide is also suited for the remote monitoring of patients from a vigilance station, since the waveguide transmits the signals without difficulties across distances of up to 50 m, without external disturbing influences and without requiring an amplification.

The invention offers great advantages when used in emergency medicine. A transmitting unit is applied on a victim of an accident still at the site of the accident, which incessantly transmits the ECG signals to the ECG device, at first in the ambulance vehicle, later on in the operating theater or in the ward.

Figure 1:
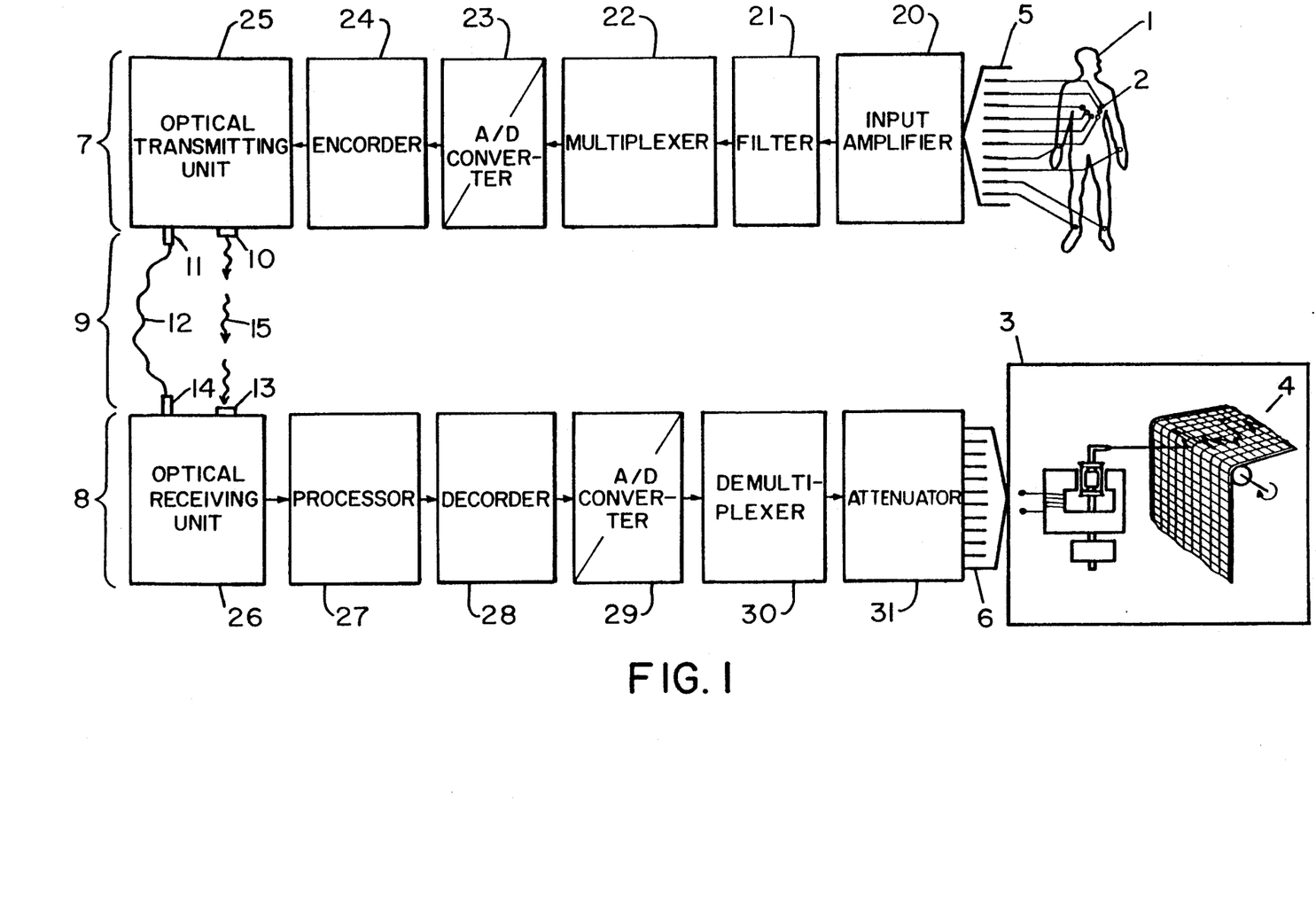
FIG. 1 is a block circuit diagram of an ECG system equipped with a device according to the invention.

FIG. 1 is a block diagram of an entire ECG system equipped with a device according to the invention. In this system, electrocardiogram signals (ECG signals) are transmitted from ECG electrodes 2 applied on the patient 1 to an ECG device 3 that processes the ECG signals and records them, as symbolized in 4. The ECG electrodes 2 are applied on the patient 1 in predefined areas that have become customary in medical practice for obtaining the so-called standard derivations "left arm, right arm, left foot, right foot, chest position 1 to 6". Two of these ECG electrodes ("left foot, right foot") serve as reference for the acquisition of the signals of the other electrodes and are hereinafter defined as first ("left foot") and second ("right foot") ECG reference electrodes. For reasons of clarity, the remaining ECG electrodes are defined as ECG signal electrodes.

In a normal customary system not using the invention, the branch 5 of output leads of the ECG electrodes 2 and the branch 6 of input leads of the ECG device 3 constitute one and the same branch: the inputs of the ECG device 3 are assigned to the ECG electrodes 2, accordingly, and designated in the corresponding way ("left arm, right arm, chest position 1 to 6"). However, if the invention is used the device according to the invention is connected between the branches 5 and 6.

The device according to the invention includes a transmitting unit 7, implied in the upper part of FIG. 1 by a curved parenthesis, and a receiving unit 8, implied in the lower part of FIG. 1 by a curved parenthesis. Between the transmitting unit 7 and the receiving unit 8 there is at least one optical link 9, implied in the central part of FIG. 1 by a curved parenthesis and explained hereinafter in further detail.

The transmitting unit 7 includes at least one modulatable optotransmitter, in the embodiment according to FIG. 1 it is two optotransmitters 10 and 11 which can be activated alternately or simultaneously. The optotransmitter 10 may consist of one or several transmitting elements and sends modulated light 15, preferentially infra-red light, into the surrounding free room. To the optotransmitter 11 a flexible optical waveguide cable 12 can be connected by means of a (not represented) disconnectable plug-in connection. The optotransmitter 11 will then feed light, preferentially infra-red light, into the connected optical waveguide cable 12. Both optotransmitters 10 and 11 are electro-optical transducers capable of converting an electric signal into modulated light and preferentially into infra-red light.

The receiving unit 8 includes at least one optoreceiver, in the embodiment according to FIG. 1 it is two optoreceivers 13 and 14 which can be activated alternately or simultaneously. The optoreceiver 13 may consist of one or several receiving elements and receives light 15, preferentially infra-red light, from the surrounding free room. To the optoreceiver 14 the flexible optical waveguide cable 12 can be connected by means of a (not represented) disconnectable plug-in connection. The optoreceiver 14 will then receive the light, preferentially infra-red light, supplied by the connected optical waveguide cable 12. Both optoreceivers 13 and 14 are electrooptical transducers capable of converting the modulation of light and preferentially of infra-red light back into a demodulated electric signal.

Thus, the optical link 9 includes alternately the free air between the optotransmitter 10 and the optoreceiver 13, or an optical waveguide designed as flexible optical waveguide cable 12. It must be understood that other embodiments of the optical waveguide, for example as single optical fibres with or without disconnectable plug-in connections are possible and can be used. It is recognizable that the transmission of signals from the transmitting unit 7 to the receiving unit 8, i.e. the transmission of ECG signals from the ECG electrodes 2 to the ECG device 3 is optical in any case, i.e. non-electrical, and alternately immaterial, i.e wireless and cable-less. Between the ECG electrodes 2 applied on the patient 1 and the ECG device 3 no electric connection is established.

In the transmitting unit 7 an input amplifier 20 is provided which hereinafter is explained in further detail in the context of FIGS. 2 and 3. The ECG signals picked off by the ECG electrodes 2 are fed to the input amplifier 20 by way of the branch 5. The input amplifier 20 possesses an assigned input channel for each ECG electrode 2, to which one assigned ECG electrode each may be connected, and guarantees the required input protection on these input channels with the help of input protection circuits that are principally known in ECG systems.

Figure 2:
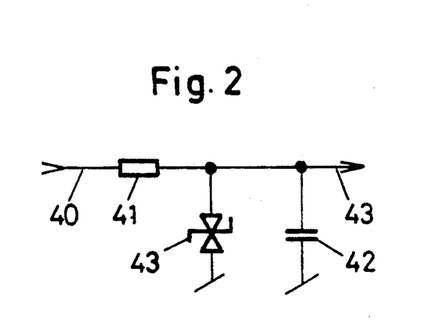
FIG. 2 is a diagrammatically represented embodiment of a input protection circuit used in the transmitting unit of the device according to the invention.

FIG. 2 is a diagrammatic representation of an embodiment of such a circuit for input protection as provided at each input channel, right at the input of the input amplifier, i.e. practically at the socket-contacts which receive the contactors of the leads of the branch 5 on the housing of the input amplifier 5. The lead 40 is connected with a lead of the branch 5. The RC element consisting of the resistor 41 and the capacitor 42 with a limit frequency of approximately 3 kHz permits that the useful signal contents penetrate while it dampens the high-frequency contents. For shielding against defibrillation impulses voltage limitation by means of the serially connected pair of Zener diodes 43 is provided, which limits the voltages that arrive at the amplifier inputs and protects the subsequent electronic circuits from being destroyed. The lead protected in such a manner leads to further signal processing in the input amplifier 20, which is now explained in further detail.

Figure 3:
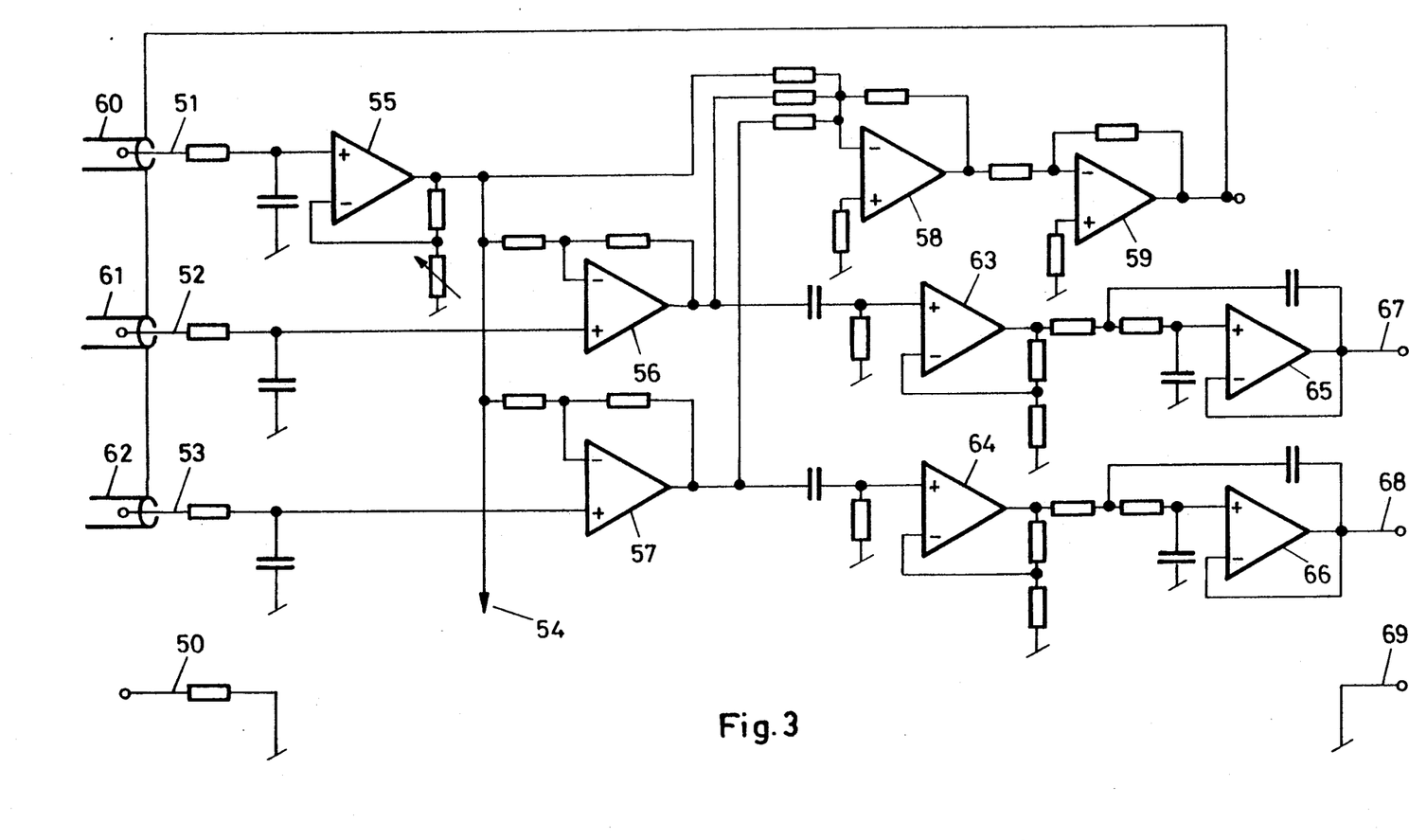
FIG. 3 is a diagrammatically represented embodiment of a circuit for preamplification, difference forming, and "antialiasing" filtration superposed to the input protection circuit and used in the transmitting unit of the device according to the invention.

Following the input protection, the input amplifier 20 forms for each signal electrode the difference between ECG signal picked up from it and the ECG signal picked up from the first ECG reference electrode ("left foot") (cf. for more information see description herinafter in connection with FIG. 3). As a consequence, each signal difference formed in this way is assigned to an ECG signal electrode. The output of the input protection circuit assigned to the second ECG reference electrode ("right foot") is connected with a common ground lead of the computing circuits in order to adapt the reference potential of the computing circuits, and of the input amplifier 20 and the transmitting unit 7 in general, to the reference potential at the patient's end.

FIG. 3 is a diagrammatic representation of an appropriate circuit for preamplification and difference forming which—as has been mentioned hereinabove—is located after the input protection circuit. It is always by way of the assigned input projection circuit (e.g. such as described in connection with FIG. 2) that the lead 50 is connected with the second ECG reference electrode ("right foot") and the lead 51 is connected with the first ECG reference electrode ("left foot"). The leads 52 and 53 are connected to one signal electrode each by way of the corresponding assigned input protection circuit and represent in FIG. 3 all remaining, not represented ECG signal electrodes, which is also implied by the arrow 54. Each ECG signal is fed to the non-inverting input of an assigned operational amplifier 55, 56, 57, etc., since it is a high-resistance input. For the appropriate forming of the desired differences all ECG signals must be amplified in its corresponding operational amplifier 55, 56, 57, etc. by the same and correct factor: on the one hand, this is reached by means of the feedback resistors at the operational amplifiers 55, 56, 57, etc. and on the other hand by adjusting the amplification with the variable resistor in the feedback loop at the operational amplifier 55. The output of the operational amplifier 55, which is assigned to the first ECG reference electrode ("left foot"), is connected by way of a resistor of the corresponding feedback chain with the inverting inputs of the operational amplifiers 56, 57, etc., which are assigned to the ECG signal electrodes (the arrow 54 symbolizes the corresponding connection with the not represented operational amplifiers).

The output of each operational amplifier 55, 56, 57 is also connected via one resistor each with the inverting input of the operational amplifier 58 so that the output of this operational amplifier 58 carries a signal representing the mean value of the ECG signals selected in such a way. Because the summation at this operational amplifier 58 is inverting, another operational amplifier 59 is provided for the inversion of the received signal which is fed to the cable shields 60, 61, 62, etc., in order to carry on their potential ("bootstrapping"). The operational amplifiers 63, 64, etc. connected as non-inverting, voltage-controlled voltage sources and serve the purpose of buffer amplification and impedance conversion. Their output leads to the operational amplifiers 65, 66, etc. connected for purposes of "antialiasing" filtration as Butterworth filters of the 2nd order. These "antialiasing" filters supply the ECG signals to be processed further on the output leads 67, 68, etc. with reference to the ground lead 69.

It is by way of one "antialiasing" filter each that is summarized in a diagrammatic way in the block 21 in FIG. 1 and whose function has been described hereinabove that the signal differences from the input amplifier 20 are fed to a multiplexer 22 which in turn passes them on to an analog-to-digital converter 23. The digital values obtained in the analog-to-digital converter 23 are encoded in an encoder 24 in the Manchester code or as FSK modulation. The purpose and the advantages of this way of encoding have already been set forth hereinabove. If necessary, an additional information for error protection is added in this place with the help of an appropriate circuit, e.g. for the cyclic redundancy check=CRC, or for the parity check according to the Hamming code.

From the output of the encoder 24 the encoded data is supplied to a modulation input of an optical transmitting unit 25 including the optotransmitters 10 and 11 and their feeder and control circuits. Thus, the modulation signal electrooptically transduced by the optotransmitters 10 and 11 corresponds to the signal differences formed in the input amplifier 20, while this modulation signal is to a large degree freed from the direct voltage content and the hum of the ECG signals as a consequence of the previous signal processing ("common mode rejection").

In the receiving unit an optical receiving unit 26 is provided including the optotransmitters 13 and 14 and their feeder and output circuits (transimpedance conversion of small currents to processable voltages). Thus, the signal electrooptically transduced by the optoreceivers 13 and 14 is demodulated in the optical receiving unit 26 and the modulation signal obtained is prepared for further use in a circuit 27: according to the frequency spectrum of the Manchester code or the FSK modulation, the continuous and low-frequency contents of the modulation signal (including the 50 Hz-hum and the 100 Hz noise by fluorescent tubes and their harmonic oscillations), and the high-frequency noise and disturbance contents are eliminated by means of filters; at the same time an amplification to the required signal value for further use takes place. Such a signal processing is principally known and does not need to be described in further detail.

The modulation signal, processed in the circuit 27 and available at one of its modulation outputs, is supplied in a decoder 28 which restores the digital values processed in the encoder 24 in the Manchester code or as FSK modulation. If necessary, a correction is made in this place with the help of an appropriate circuit and with the help of the additional information for error protection added in the transmitting unit.

The digital values obtained in this way are fed to a digital-to-analog converter 29 in order to regain the analog signals. During the simultaneous smoothing of the analog signals (low-pass filtration) an interpolation of the support values takes place, which causes the correction of the time displacement due to multiplexing.

Hence, the analog signals are made isochronic again and by this it becomes possible to supply them isochronically to the ECG device.

The analog signals obtained and processed in this way are supplied to a demultiplexer 30. It is equipped with outputs each of which is assigned to a signal difference formed in the input amplifier 20 of the transmitting unit 7. The signals from these outputs of the demultiplexer 30 are still attenuated in a circuit 31 to values that correspond to the normal values of the real ECG signals picked off directly at the ECG electrodes 2, thus permitting to feed them directly to the corresponding inputs of the ECG device 3 by way of the branch 6. However, since only the ECG signals from the ECG signal electrodes are transmitted via the optical link 9 and supplied to the corresponding inputs of the ECG device ("left arm, right arm, chest position 1 to 6") by way of the branch 6, the potential at the remaining inputs of the ECG device ("right foot, left foot") does not make any useful contribution; for this reason, these two last inputs are connected to the reference potential of the ECG device (in a not represented way).

As can be seen, the transmission of the ECG signals by way of the optical link 9 is effectuated serially as one-way transmission data towards ECG device, both the encoder 24 and the decoder 28 being intended and designed for the processing of the Manchester code or the frequency shift keying modulation.

Figure 4:
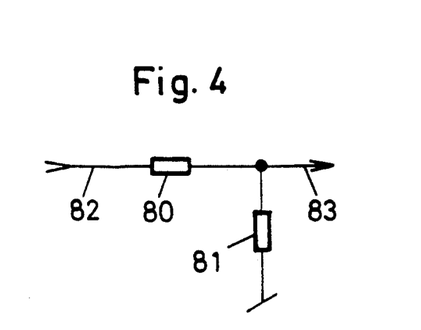
FIG. 4 is a diagrammatically represented embodiment of an output circuit used in the receiving unit of the device according to the invention.

FIG. 4 is a diagrammatic representation of an embodiment of an output circuit used in the receiving unit of the device according to the invention, which is represented in a symbolic way in the block 31 of FIG. 1. Since the transmitted and thereupon decoded signals already correspond to the desired signals, only their value has to be adjusted in a way that the ECG device does not "note" any difference, whether the patient is connected directly by the customary cables or by the device according to the invention. This requires only a linear attenuation achieved by means of the represented potentiometer-type resistor with the resistors 80, 81. The input lead 82 of this circuit is connected with one of the outputs of the demultiplexer 30 and the output lead 83 is linked with one of the corresponding inputs of the ECG device ("left arm, right arm, chest position 1 to 6") by way of a lead of the branch 6.

In a modification, the transmitting unit 7 may be designed as independent integrated device which the patient can carry, for example, at the belt, on the back or strapped to him/her in another fashion.

Figure 5:
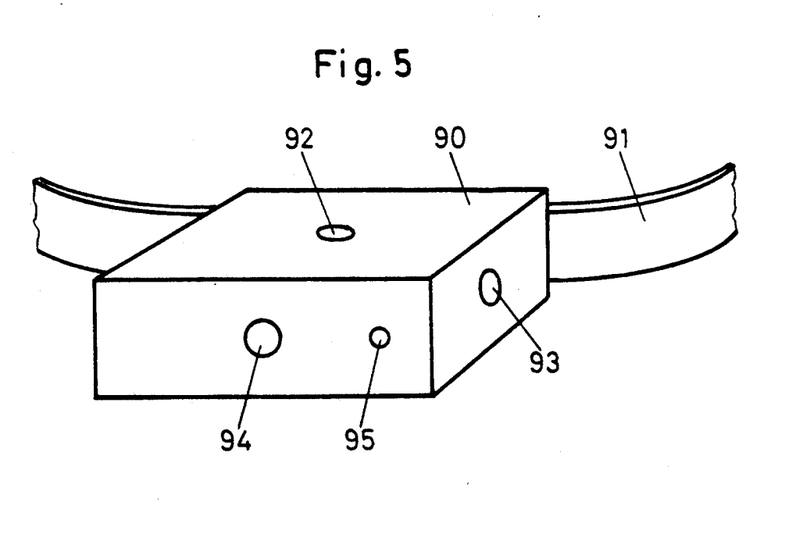
FIG. 5 is a diagrammatically and perspectively represented embodiment of the housing of a transmitting unit equipped with optotransmitters and used in the device according to the invention.

FIG. 5 is a diagrammatic and perspective representation of a housing 90 of such a transmitting unit 7, which may be carried by means of a belt 91. This housing 90 is equipped with one or several, for example four optotransmitters 92, 93, 94 (the fourth is not visible in FIG. 5). These optotransmitters are for instance infra-red transmitters and are located at the sides of the transmitting unit 7, or of its housing 90, not facing the patient, for example one each at the upper and at the three non-engaged lateral walls of the housing 90. At the housing 90, a socket 95 for the connection of a flexible waveguide cable 12 is provided.

In a modification, the transmitting unit 7 may be designed as independent two-part device. One part is an operating unit which the patient may carry at the belt, in the pocket, or strapped to him/her in another fashion. The other part is an optotransmitter portable unit which may be carried by the patient as headband.

Figure 6:
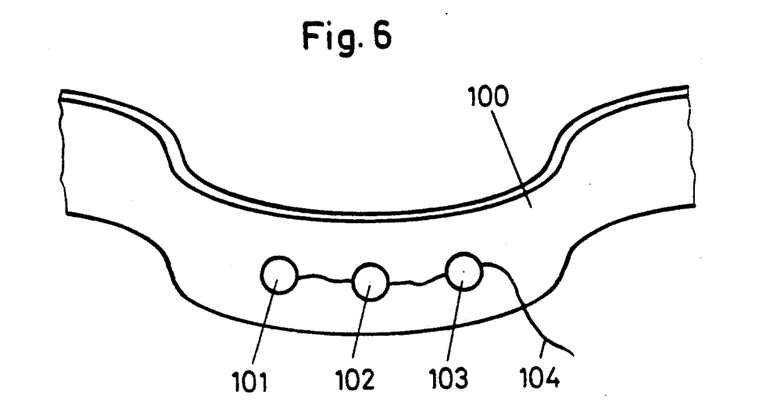
FIG. 6 is a diagrammatically and perspectively represented embodiment of a headband equipped with optotransmitters and used in the device according to the invention.

FIG. 6 is a diagrammatic and perspective representation of such a headband 100 having herein three optotransmitters 101, 102, 103 on its side not facing the patient. The optotransmitters 101, 102, 103 are linked with each other and with the operating unit by means of the thin cable 104. The cable 104 can hardly affect the patient, for its two ends are connected to parts which the patient is carrying with him/her. The operating unit has not been represented because in a possible embodiment it is very similar to the transmitting unit 7 represented in FIG. 5, for example, its housing is the same as the housing 90 represented in FIG. 5, just without the optotransmitters.

For receiving the radiation emitted by these optotransmitters at least one and preferentially several optoreceivers are arranged in one or several fixed locations of a room surrounding the patient, for example in the middle of two or three walls of the room, where the patient is, or even at the ECG device itself.

The description as set forth hereinabove concerning ten transmission channels as in electrocardiography with twelve standard derivations, can easily be adapted to another multiplicity of channels, for example to the twenty-two to twenty-four channels needed in electroencephalography.

The description as set forth hereinabove concerning optical transmission can also be adapted easily to another kind of electromagnetic transmission of microwaves, as is well-known in the state of the art of telecommunications.

In general, the embodiment of the invention is by no means limited to the method as hereinabove set forth as a mere example and the corresponding device. Many equivalent methods and devices whose embodiment is within the scope of this invention are known to those skilled in the art.

We claim:

1. A method for the transmission of bioelectric potential differences, such as electrocardiogram signals, occurring between more than two electrodes applied on a patient, from the patient to an ECG device supplying twelve standard derivations, in the course of which at least ten ECG electrodes are applied on the patient in the customary way for obtaining the standard deviations, two of said at least ten ECG electrodes are defined as first and second ECG reference electrodes and the remaining ECG electrodes as ECG signal electrodes, the transfer of potential differences between the patient and the ECG device being effectuated as an electromagnetic one-way connection between the electrodes and the ECG device, said method comprising the steps of:

calculating the difference between an ECG signal obtained from each ECG signal electrode and an ECG signal obtained at the first ECG reference electrode yielding signals that are essentially free from any component corresponding to a common direct voltage content and also free from any component corresponding to a hum, determining a reference potential at the patients' end from the second ECG reference electrode, transmitting the signals in a one-way serial manner, said step of transmitting the signals comprises the steps of:

multiplexing the signals to the transmitted, converting the multiplex signal from an analog to digital signal, encoding the digital signal using Manchester encoding or frequency shift keying-modulation, modulating a light beam with the encoded signal transmitting the modulated light beam to a receiving unit, demodulating the modulated light beam to obtain the encoded signal, converting the digital encoded signal into an analog encoded signal, and demultiplexing the analog encoded signal to obtain transmitted ECG signals; and inputting the transmitted ECG signals to the corresponding inputs of the ECG device, said reference potential is supplied to the remaining inputs of the ECG device.

2. The method according to claim 1, wherein the transmission is performed optically and via an optical waveguide.

3. The method according to claim 1, further comprising the step of adding additional information to the encoded signal for error protection in transmission.

4. The method according to claim 3, further comprising the step of correcting the decoded signal by removing the additional information added to the encoded signal.

5. A device for the transmission of bioelectric potential differences occurring between more than two electrodes applied on a patient to an ECG device in an ECG system comprising at least ten ECG electrodes applied on a patient and an ECG device for twelve standard derivations, while two specific ECG electrodes are defined as first and second ECG reference electrodes and the remaining ECG electrodes as ECG signal electrodes, having a transmitting unit, a receiving unit, and at least one optical link in between, the transmitting unit including:

input protection circuits to which one assigned ECG electrode each can be connected, means for computing the difference between signals from respective input protection circuits, one of said input protection circuits being assigned to an ECG signal electrode and a second one of said input protection circuits being assigned to the first ECG reference electrode so that each signal difference is assigned to an ECG signal electrode, the output of one of said input protection circuits assigned to the second ECG reference electrode is connected with a common ground lead to the means for computing, a multiplexer for multiplexing the obtained signal differences, at least one modulatable optotransmitter having a modulation input through which the output of the multiplexer is linked via the serial connection of an analog-to-digital converter, and an encoder, and the receiving unit including:

at least one optoreceiver having an output for the output of the modulation of a received light beam, a demultiplexer having an input linked to the output of said at least one optoreceiver, said demultiplexer is connected in series to a decoder and a digital-to-analog converter, the outputs of the digital-to-analog converter, each of which the assigned to the signal difference formed in the transmitting unit, are connected to a corresponding input of the ECG device.

6. The device according to claim 5, further comprising:

a first circuit means for adding additional information to an output of said encoder for error protection in transmission; and correction circuit means for removing the additional information added to the output of said encoder from the output of said demultiplexer.

7. The device according to claim 5, wherein the transmitting unit is designed to be carried by the patient as an independent portable device comprising at least one opto-transmitter arranged on a side of the transmitting unit which faces away from the patient when the transmitting unit is carried by the patient, and at least one opto-receiver arranged at a fixed location within a room surrounding the patient.

8. The device according to claim 5, wherein the transmitting unit is designed to be carried by the patient as an independent, two-part, portable device comprising a portable operating unit, a portable opto-transmitter unit, the opto-transmitter unit comprising at least one opto-transmitter arranged on a side of the opto-transmitter unit which is facing away from the patient when the opto-transmitter unit is carried by the patient, and an opto-receiver arranged at a fixed location within a room surrounding the patient.

* * * * *